United States Patent
Nakaya et al.

(10) Patent No.: US 7,796,797 B2
(45) Date of Patent: Sep. 14, 2010

(54) APPARATUS FOR OBTAINING AN IMAGE OF A BLOOD CELL AND METHOD FOR OBTAINING AN IMAGE OF A BLOOD CELL

(75) Inventors: Masanori Nakaya, Kobe (JP); Ryuichi Tohma, Akashi (JP)

(73) Assignee: Sysmex Corporation (JP)

( * ) Notice: Subject to any disclaimer, the term of this patent is extended or adjusted under 35 U.S.C. 154(b) by 991 days.

(21) Appl. No.: 11/528,757

(22) Filed: Sep. 28, 2006

(65) Prior Publication Data

US 2007/0076190 A1  Apr. 5, 2007

(30) Foreign Application Priority Data

Sep. 28, 2005 (JP) .............................. 2005-282291
Sep. 29, 2005 (JP) .............................. 2005-285067

(51) Int. Cl.
*G06K 9/00* (2006.01)
*G01N 33/48* (2006.01)

(52) U.S. Cl. ........................................ 382/134; 356/39

(58) Field of Classification Search ................ 382/128, 382/129, 130, 131, 132, 133, 134; 424/1.17, 424/529, 569; 435/70.4, 355, 372; 436/520, 436/521, 522; 356/39; 600/454, 465, 468, 600/480, 500; 702/21

See application file for complete search history.

(56) References Cited

U.S. PATENT DOCUMENTS

| 7,344,890 | B2 * | 3/2008 | Perez et al. ................... 436/63 |
| 7,346,200 | B1 * | 3/2008 | Tsipouras et al. ........... 382/128 |
| 7,354,775 | B2 * | 4/2008 | Yoshida et al. .............. 436/522 |
| 7,415,148 | B2 * | 8/2008 | Wrigglesworth et al. ..... 382/133 |
| 7,521,243 | B2 * | 4/2009 | Lindberg et al. ............. 436/10 |
| 7,522,758 | B2 * | 4/2009 | Ortyn et al. ................. 382/133 |

FOREIGN PATENT DOCUMENTS

JP          60-162955          8/1985

* cited by examiner

*Primary Examiner*—Abolfazl Tabatabai
(74) *Attorney, Agent, or Firm*—Brinks Hofer Gilson & Lione

(57) ABSTRACT

A apparatus for obtaining an image of a blood cell is described, a representative one of which includes image obtainer for obtaining an image of a predetermined blood cell in a blood sample smeared on a sample holder; an analysis result obtainer for obtaining an analysis result of the blood sample; and a controller for controlling the image obtainer such that the image obtainer obtains the image under a first imaging condition when the analysis result does not indicate a presence of a predetermined anomalous cell, and obtains the image under a second imaging condition to be different from the first imaging condition when the analysis result indicates the presence of the predetermined anomalous cell.

20 Claims, 18 Drawing Sheets

[Fig. 1]
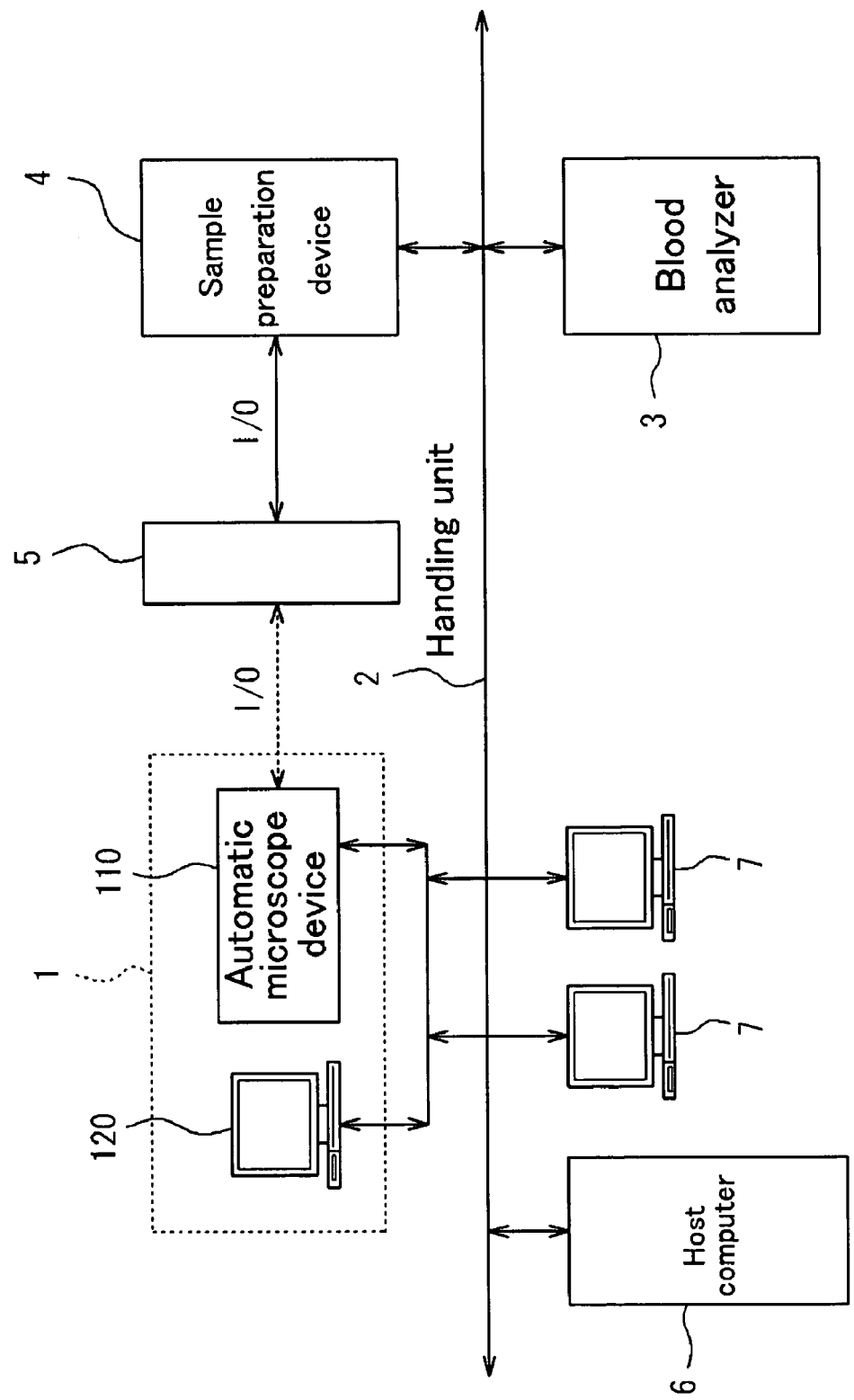

[Fig. 2]
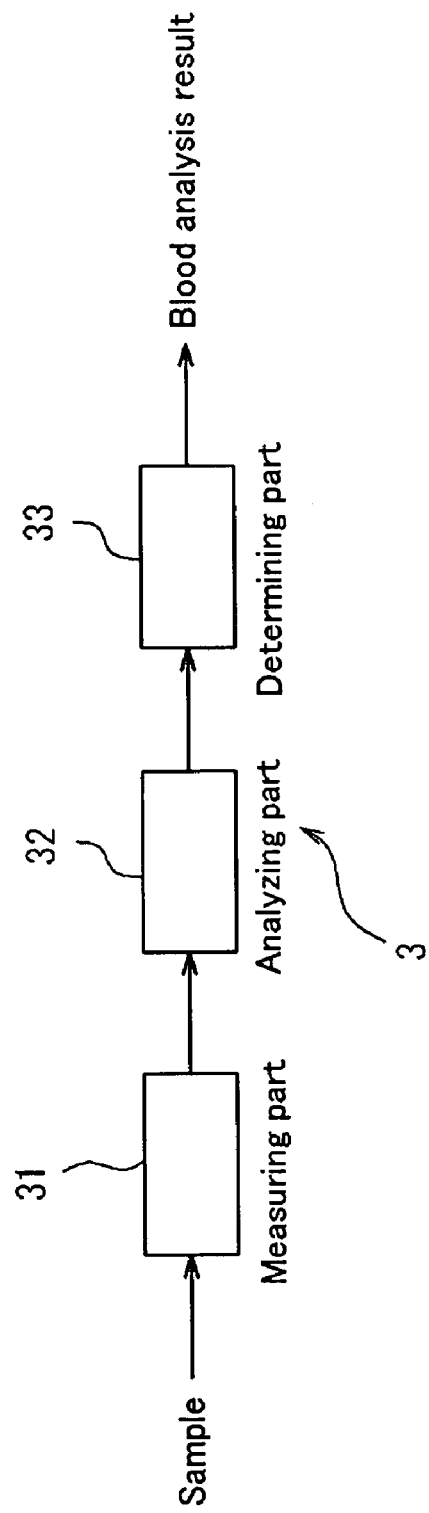

[Fig. 3]

| ITEM | | Determination method |
|---|---|---|
| ⟨Abnormal⟩ | | |
| WBC Abn Scattergram | | Determined from WBC/BASO scattergram, DIFF scattergram |
| NRBC AbnScattergram | | Determine from NRBC scattergram |
| Neutropenia | W | NEUT #⟩⟨10.0×10$^2$/μL (or% set) |
| Neutrophilia | W | NEUT #⟩⟩110.0×10$^2$/μL (or% set) |
| Lymphopenia | W | LYMPH #⟨⟨8.0×10$^2$/μL (or% set) |
| Lymphocytosis | W | LYMPH #⟩⟩40.0×10$^2$/μL (or% set) |
| Monocytosis | W | MONO #⟩⟩10.0×10$^2$/μL (or% set) |
| Eosinophilia | W | EO #⟩⟩7.0×10$^2$/μL (or% set) |
| Basophilia | B | BASO #⟩⟩2.0×10$^2$/μL (or% set) |
| Leukocytopenia | B | WBC⟨⟨25.0×10$^2$/μL (or% set) |
| Leukocytosis | C | WBC⟩180.0×10$^2$/μL (or% set) |
| NRBC present | C | NRBC% ⟩ 2% |
| ⟨Suspect⟩ | | |
| Blasts? | | Determine from patterns of DIFF scattergram, IMI scattergram |
| Immature Gran? | | Determine from patterns of DIFF scattergram, IMI scattergram |
| Left Shift? | | Determine from patterns of DIFF scattergram, IMI scattergram |
| Atypical Lympho? | | Determine from patterns of DIFF scattergram, IMI scattergram |
| Abn Lympho/L-Blasts? | | Determine from patterns of DIFF scattergram, IMI scattergram |
| NRBC? | | Determine from DIFF scattergram |
| RBC Lyse resistance? | | Numeric calculation |

[Fig. 4]

| | ITEM | Determination method |
|---|---|---|
| | <Abnormal> | |
| | RBC Abn Distribution | Numerical calculation and size comparison |
| | Dimorphic Population | Determine by shape near peak size distribution, peak and trough difference |
| | RET Abn Scattergram | Determine from RET scattergram |
| R | Reticulocytosis | RET%>5.0% or RET#>20.0×10$^4$/μL |
| | Anisocytosis | RDW-SD>65fL or RDW-CV>20% |
| | Microcytosis | MCV<70fL |
| B | Macrocytosis | MCV>110fL |
| | Hypochromia | MCHC<29.0g/dL |
| | Anemia | HGB<10.0g/dL |
| C | Erythrocytosis | RBC>650×10$^4$/μL |
| | <Suspect> | |
| | RBC Agglutination? | Numerical calculation and size comparison |
| | Turbidity/HGB Interference? | MCHC>36.5g/dL |
| | Iron Deficiency ? | Numerical calculation and size comparison |
| | HGB Defect? | Numerical calculation and size comparison |
| | Fragments? | Determine from RET scattergram, Numerical calculation and size comparison |

[Fig. 5]

| | ITEM | Determination method |
|---|---|---|
| P | <Abnormal> PLT Abn Scattergram | Determine from RET scattergram |
| | PLT Abn Distribution | Numerical calculation and size comparison |
| L | Thrombocytopenia Thrombocytosis | RLT<6.0×10$^4$/μL  RLT>60.0×10$^4$/μL |
| T | <Suspect> PLT Clumps? | Determine from DIFF, IMI, NRBC scattergrams |
| | PLT Clumps (S) ? | Numeric calculation and size comparison |

[Fig. 6]
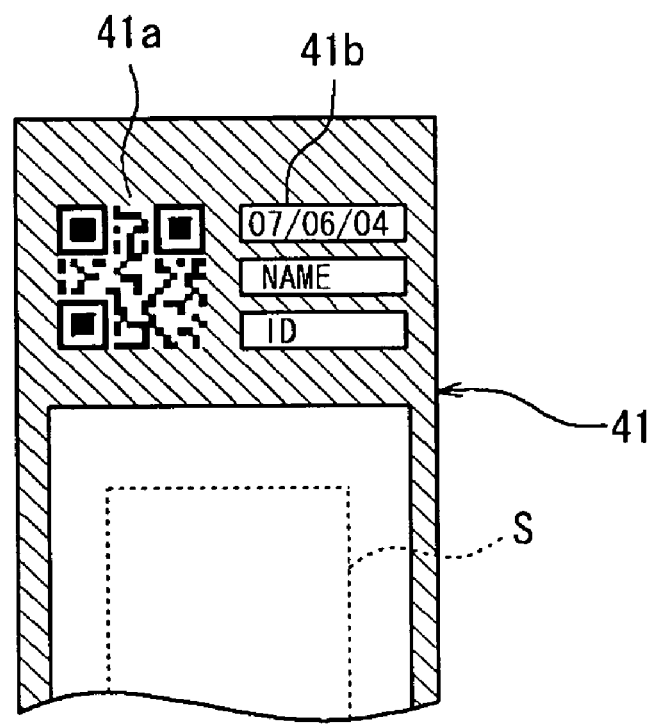

[Fig. 7]
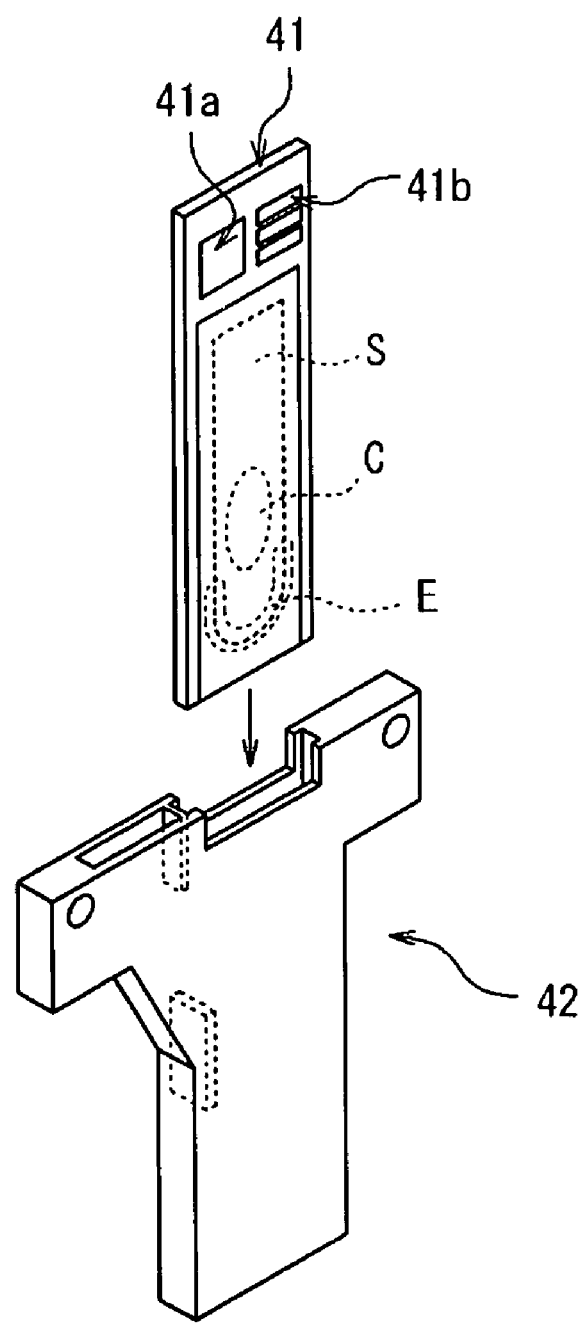

[Fig. 8]
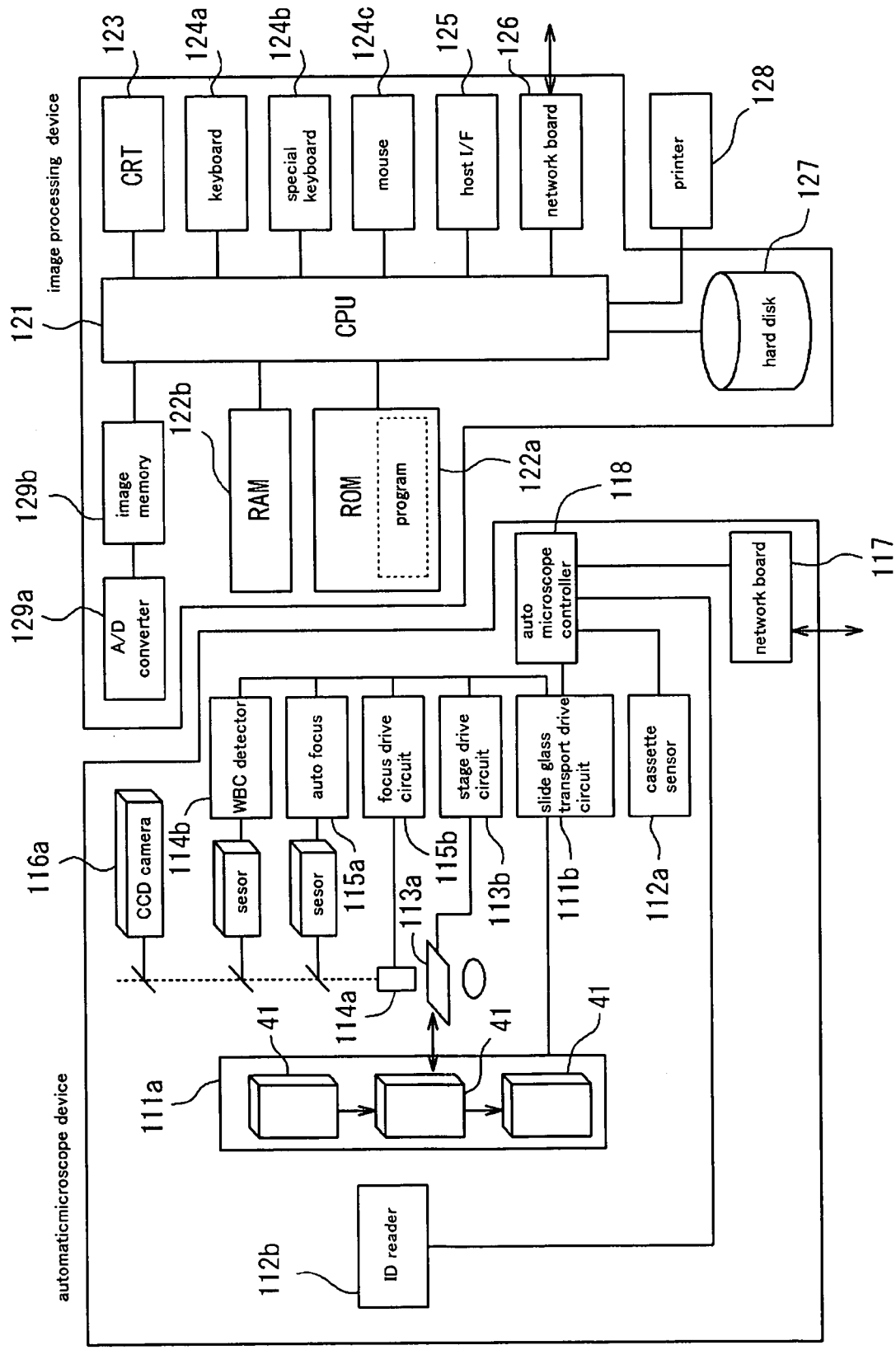

[Fig. 9]
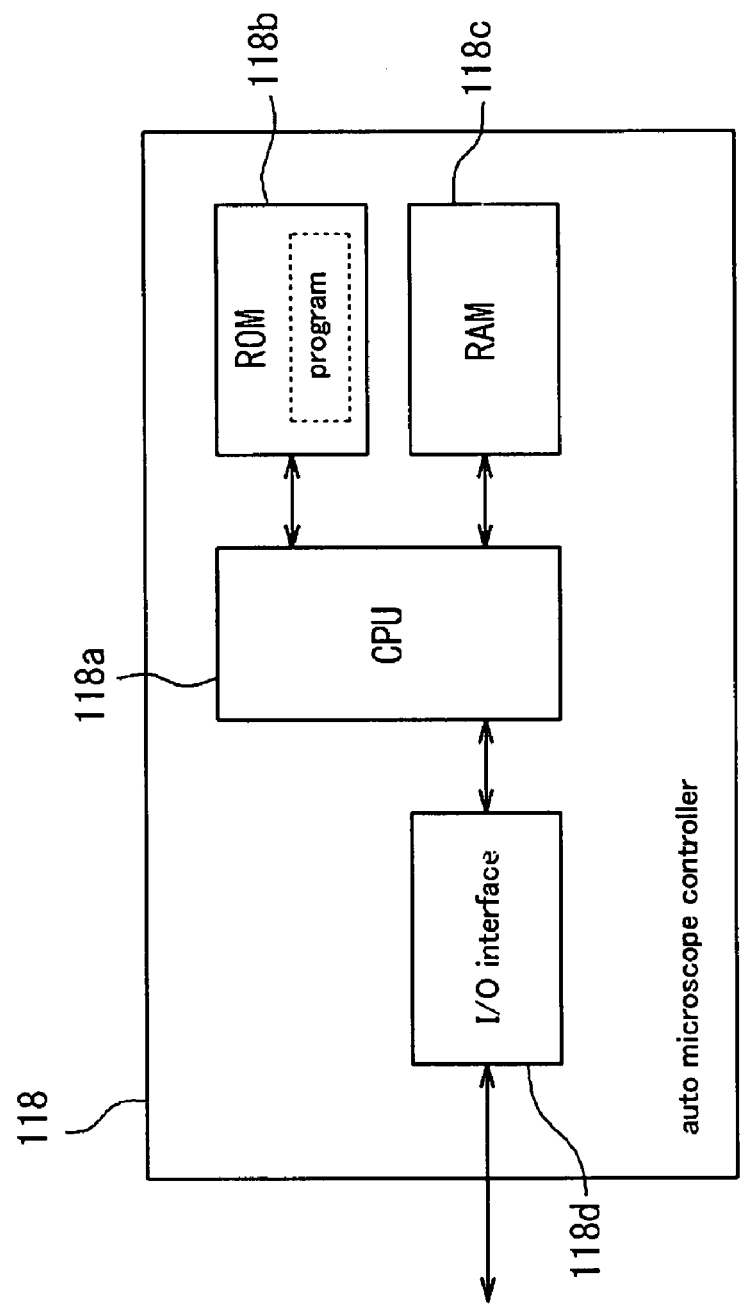

[Fig. 10]
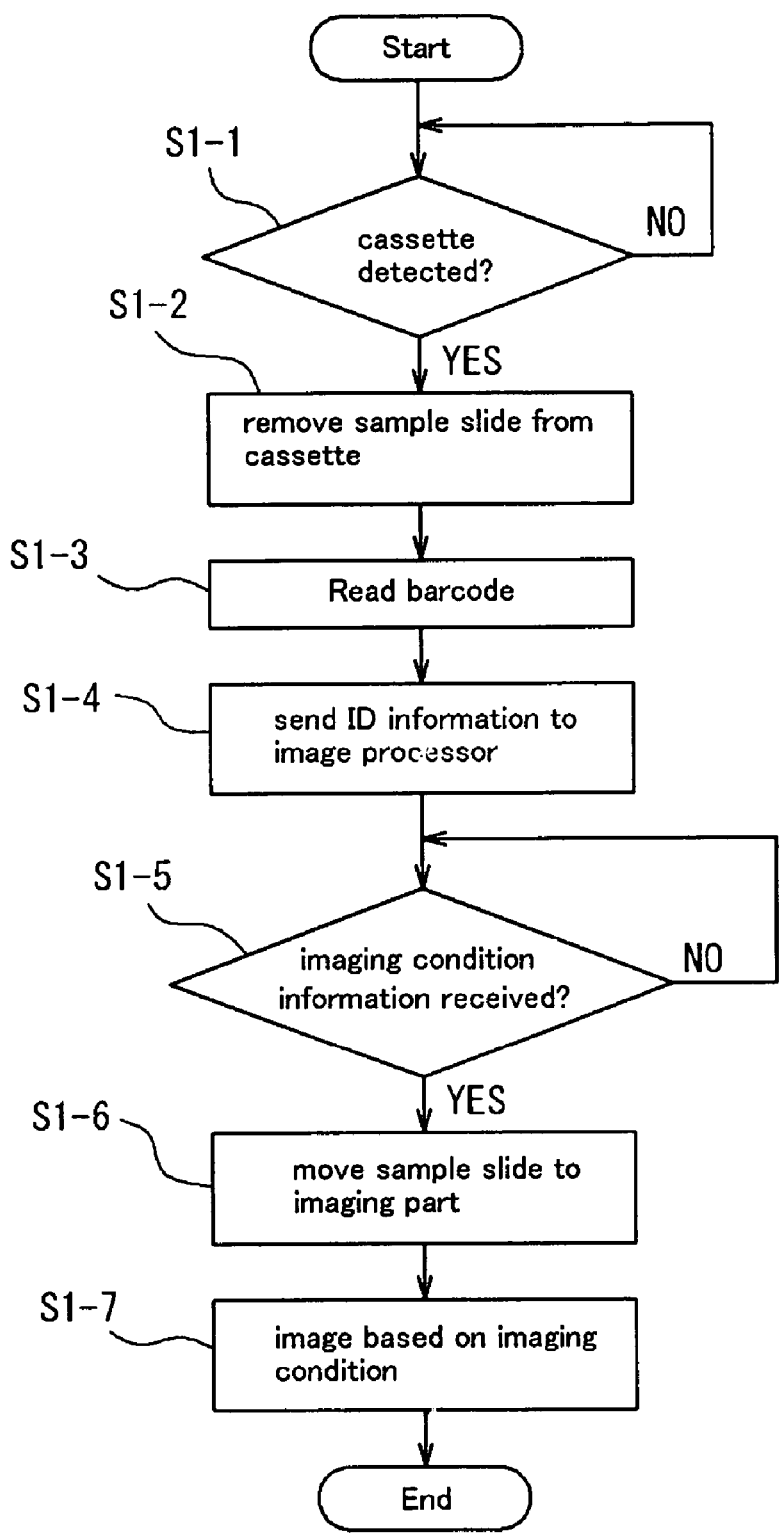

[Fig. 11]
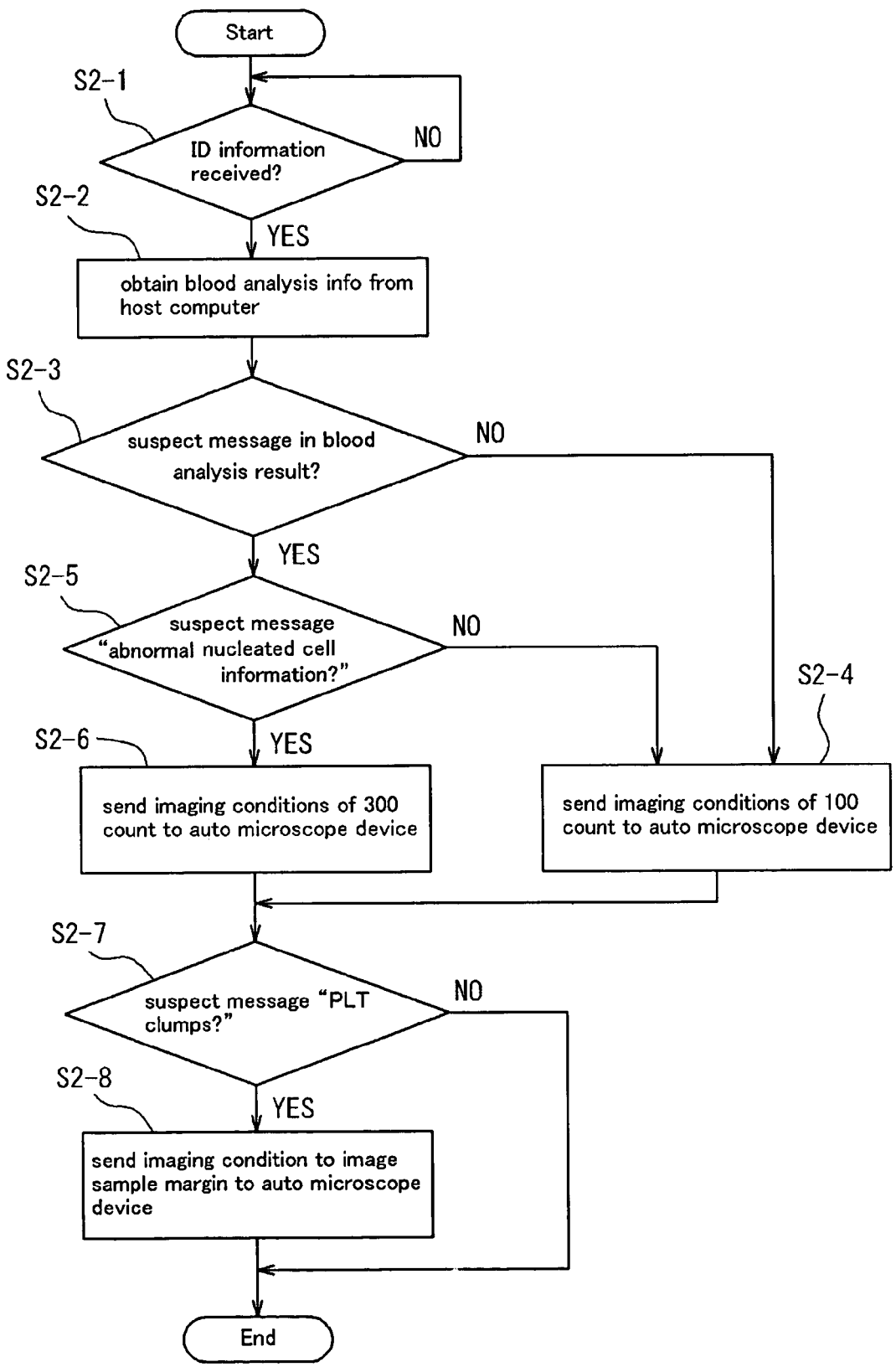

[Fig. 12]
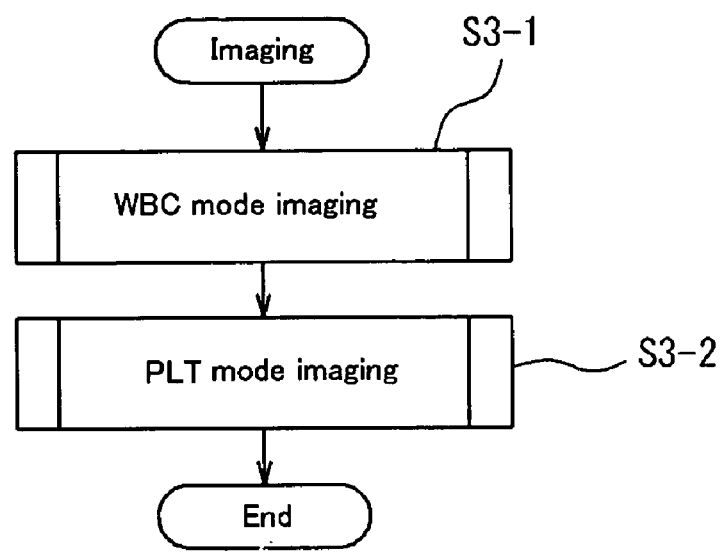

[Fig. 13]
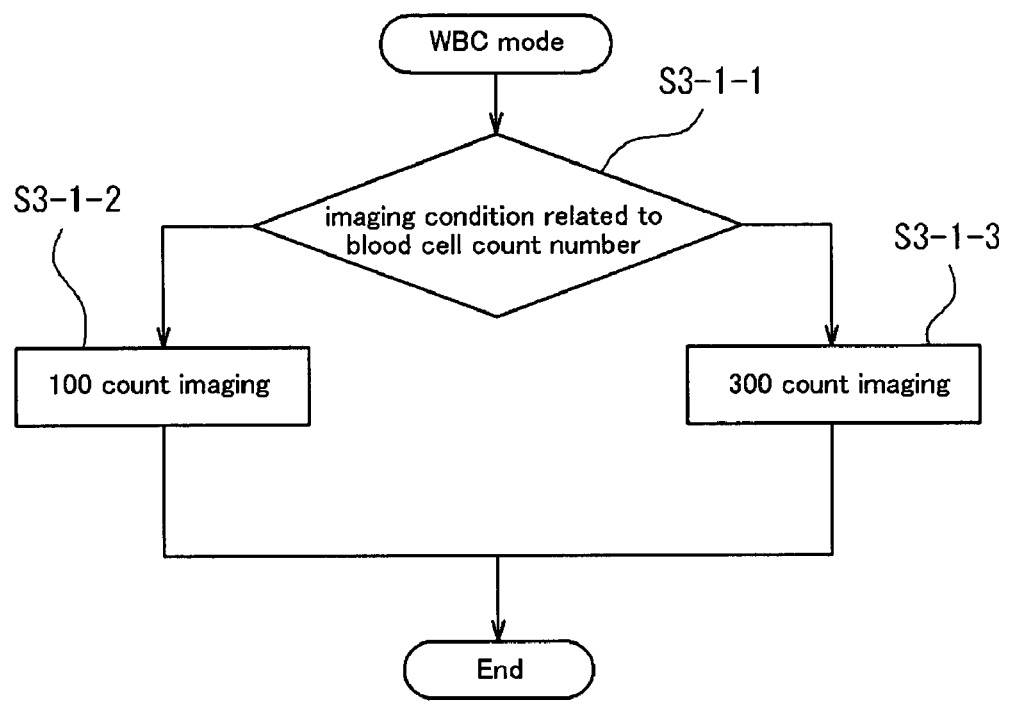

[Fig. 14]
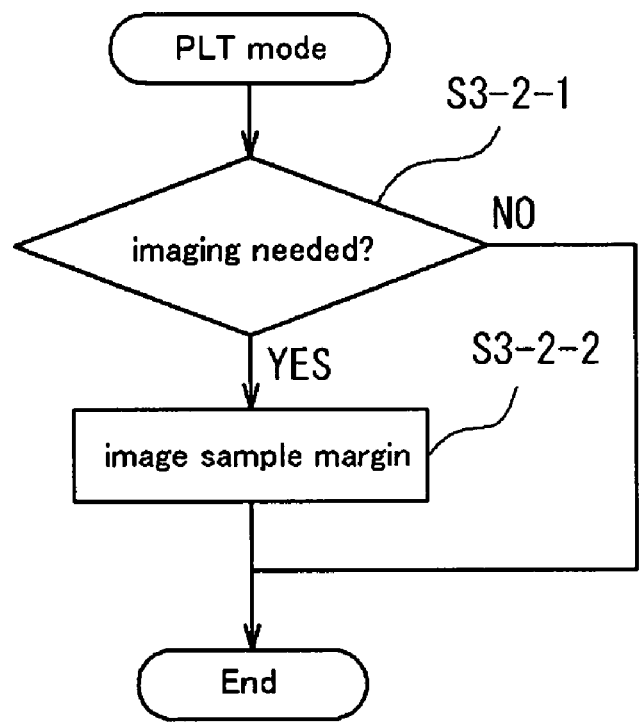

[Fig. 15]
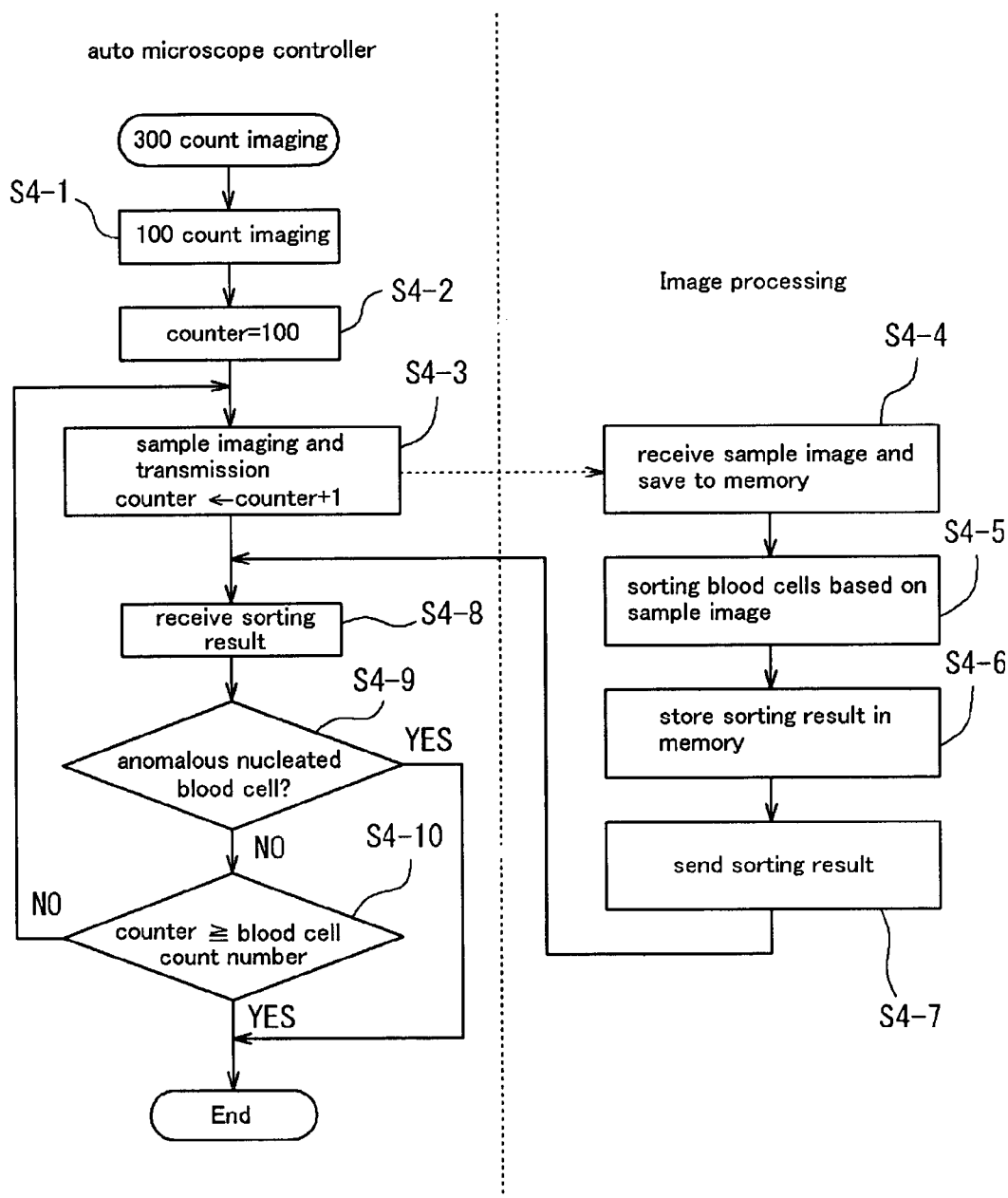

[Fig. 16]
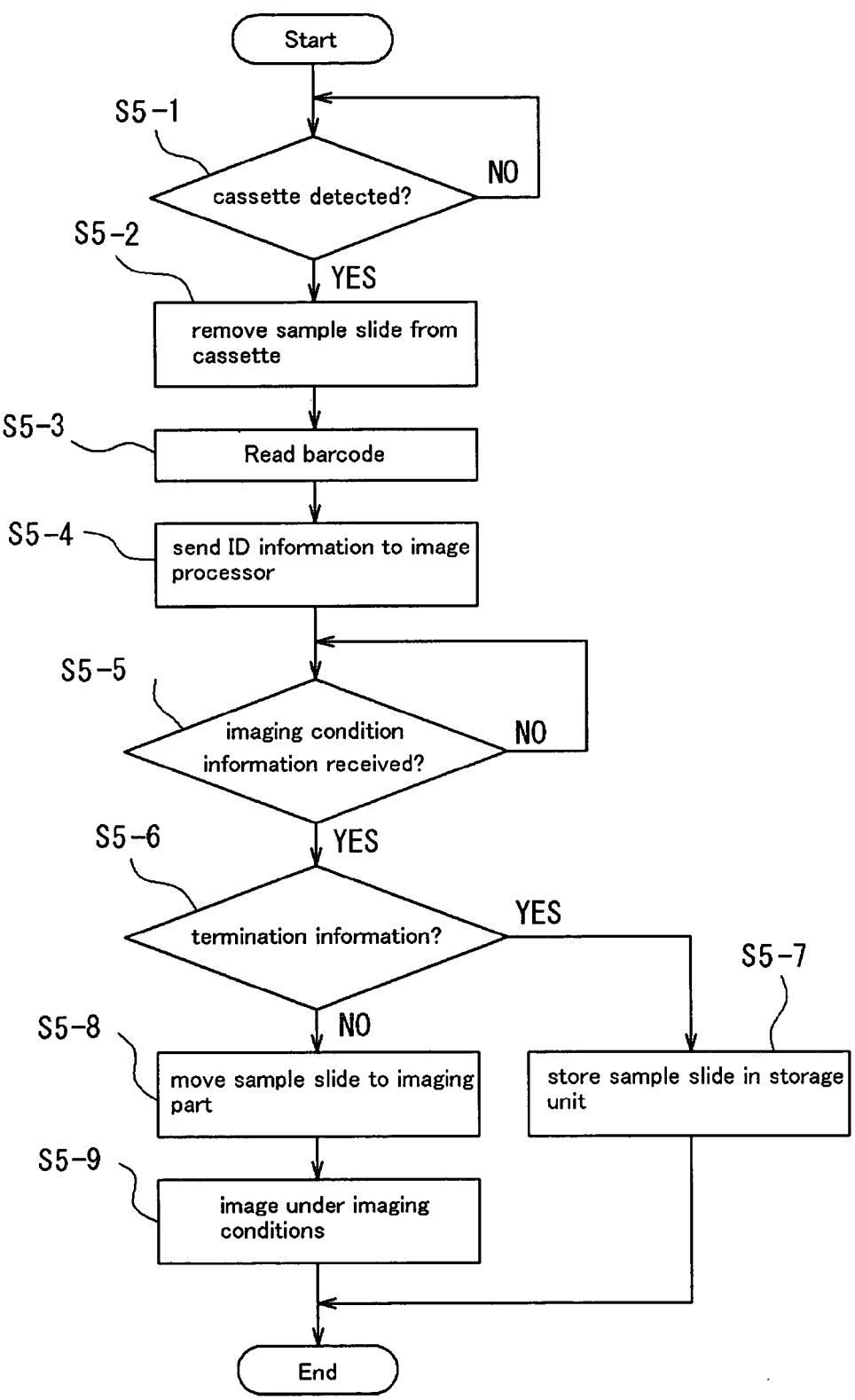

[Fig. 17]
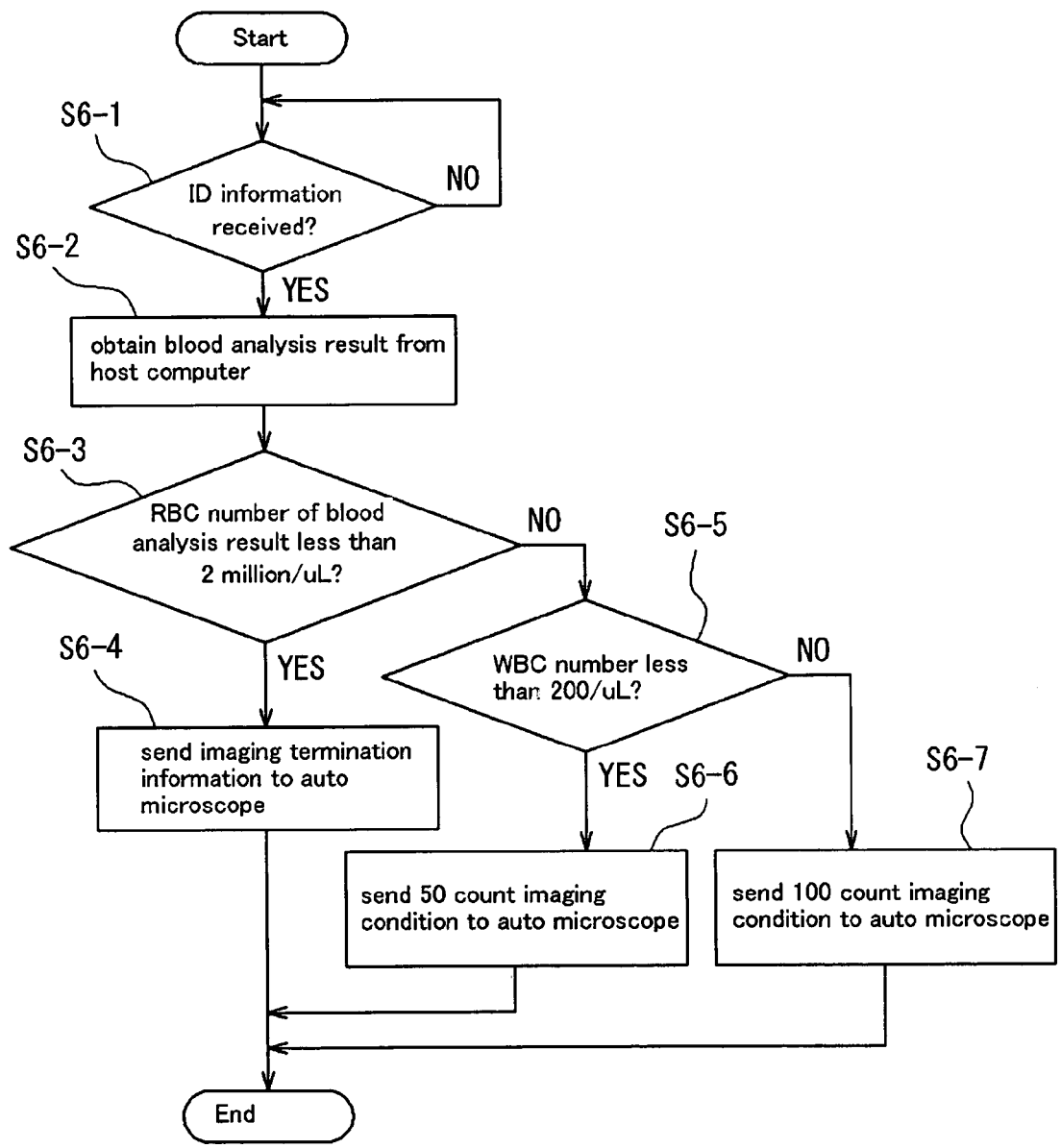

[Fig. 18]
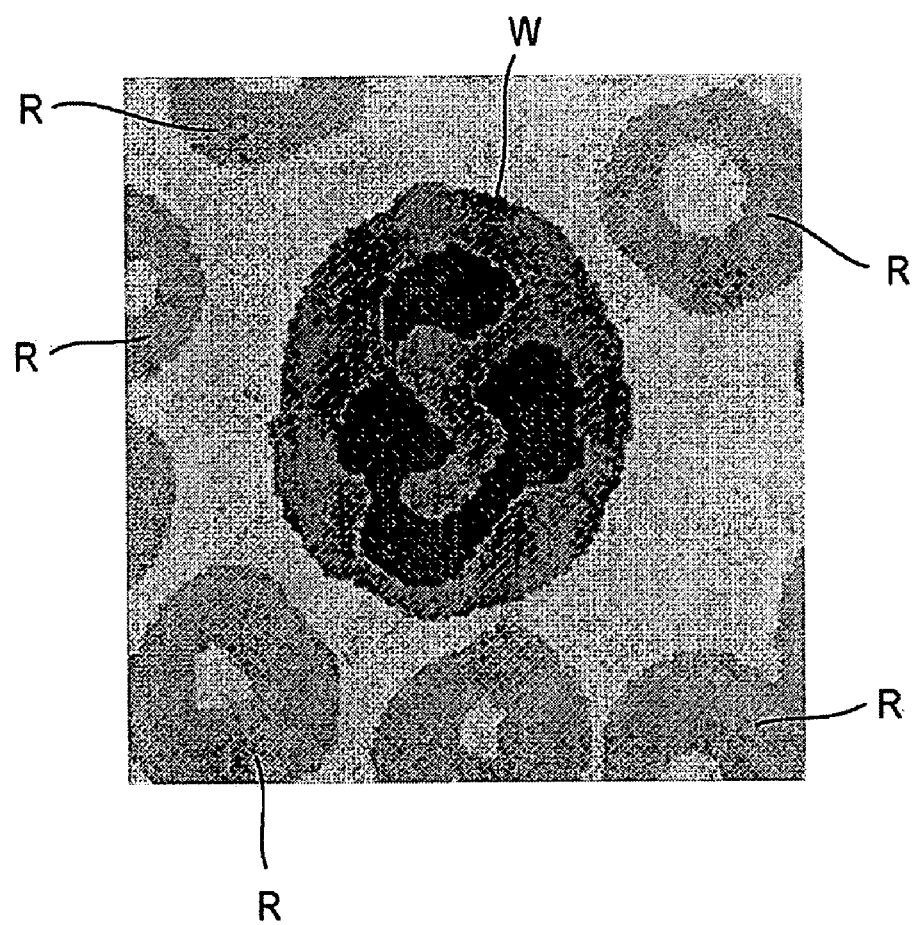

APPARATUS FOR OBTAINING AN IMAGE OF A BLOOD CELL AND METHOD FOR OBTAINING AN IMAGE OF A BLOOD CELL

This application claims priority under 35 U.S.C. §119 to Japanese Patent Application Nos. JP2005-282291 filed Sep. 28, 2005 and JP2005-285067 filed Sep. 29, 2005, the entire content of which is hereby incorporated by reference.

FIELD OF THE INVENTION

The present invention relates to an apparatus for obtaining an image of a blood cell and a method for obtaining an image of a blood cell.

BACKGROUND OF THE INVENTION

Japanese Laid-Open Patent Publication No. 60-162955 discloses an automatic analysis device for blood cells capable of automatically and simultaneously performing blood cell calculations and morphological cell classifications from the same sample.

This automatic cell analysis device is provided with an automatic cell classifying system for preparing a blood preparation by smearing a slide glass with blood from a blood sample and staining the smear then identifying and classifying blood cell images of a blood preparation, and an automatic cell calculating system for counting the number of blood cells in a fixed quantity of the blood cell sample, and the device simultaneously reports the blood cell calculation and blood cell classification results.

More specifically, in this blood cell analysis device, a preparation is enlarged by an optical microscope, a blood cell image is obtained with a camera, blood cell characteristics are calculated by a characteristic extraction circuit, and each type of blood cell is classified. Then, this blood cell analysis device counts the blood cells based on detection signals for hemoglobin concentration, white blood cells, red blood cells, and platelets.

In this blood cell analyzing device, when the blood cell count exceeds a normal range set beforehand in a microcomputer, a signal is sent from the microcomputer to an I/O controller as an abnormal value of the suspicious sample.

The I/O controller designates that the blood cell number of the blood cell classification is two or three times higher for a confirmed abnormal sample and for an ID preparation matching such a sample, or changes the blood cell examination method of the preparation to a method for detailed examination of a specific area having a high percentage of abnormal cells at an end part of the smear surface so as to increase abnormal cell detection sensitivity.

In this blood cell analyzing device, an abnormal cell is determined based on the "cell number" calculation information, the number of cells of the blood cell classification is designated two or three times higher, or changes the blood cell examination method for the preparation, however, a problem arises inasmuch as the abnormal sample determination via the number of blood cells may not have suitable condition settings for the designated blood cell numbers and the changed blood cell examination method.

Specifically, when a sample is determined to be abnormal based on the blood cell count, a sample which has abnormal blood cells but the blood cell count is normal can not be determined as an abnormal sample, such that the conditions can not be suitably changed.

Further, when a sample is determined to be abnormal based on a "blood cell count," a sample that is normal is normal but has a blood cell count that somewhat exceeds the normal range with the appearance of abnormal cells may be determined to be an abnormal sample, such that the condition are unsuitably set.

That is, the blood cell count is one standard for determining an abnormal sample (for example, there may be suspicion of leukemia when the white blood cell count exceeds a normal number), but the blood cell count is not direct information indicating the possibility of the occurrence of abnormal cells in a sample, and is not a reliably standard for determining whether or not a sample is abnormal.

That is, even when the white blood cell count is increased for leukemia, the white blood cell count may be reduced to the normal range by chemotherapy or the like. In this case, conditions must be set for blood classification so that an abnormal sample has abnormal blood cells even when the number of white blood cells is in the normal range.

A white cell count that exceeds the normal range may occur even in healthy people without leukemia depending on their condition, and it is not desirable that the blood classification condition settings should unsuitably determine these as abnormal samples when the condition settings for blood classification might determine them as normal samples.

In the above automatic blood cell analyzer, when the number of blood cells exceeds the normal range, the blood cell count for blood cell classification is increased two or three fold, to make the blood cell count less than the normal range and other measures are not performed.

However, the following problems arise when the blood cell number is less than the normal range.

For example, in an automatic blood cell analyzer, a predetermined number (for example 100) of white blood cells must be imaged to classify white blood cells, and if there is a sufficient abundance of white blood cells in a sample, the white blood cells for imaging can be easily retrieved and imaged in a short time.

However, when a predetermined number of white blood cells must be imaged and there are few white blood cells in a sample, a long time is required to retrieve the required number of white blood cells in the sample, thereby lengthening the imaging time. Moreover, when the required number of white blood cells are not present in the sample, the imaging process is not completed.

Additionally, when imaging blood imaging is performed with auto focusing of the optical microscope using the red blood cell, which are the most prevalent component in the sample, as a standard; however, when there are very few red blood cells, such auto focusing can not be performed.

SUMMARY OF THE INVENTION

The scope of the present invention is defined solely by the appended claims, and is not affected to any degree by the statements within this summary.

An object of the present invention is to set optimum imaging conditions to efficiently perform imaging of blood cells based on blood analysis result.

The apparatus for obtaining an image of a blood cell of a first aspect of the present invention includes: (a) an image obtainer for obtaining an image of a predetermined blood cell in a blood sample smeared on a sample holder; (b) an analysis result obtainer for obtaining an analysis result of the blood sample; and (c) a controller for controlling the image obtainer such that the image obtainer obtains the image under a first imaging condition when the analysis result does not indicate a presence of a predetermined anomalous cell, and obtains the image under a second imaging condition to be different from the first imaging condition when the analysis result indicates the presence of the predetermined anomalous cell.

The method for obtaining an image of a blood cell of a second aspect of the present invention includes: (a) obtaining a blood analysis result of a blood sample; and (b) obtaining an imaging of a predetermined anomalous cell in a blood sample smeared on a sample holder; wherein the image is obtained under a first imaging condition when the analysis result dose not indicate a presence of a predetermined anomalous cell, and obtained under a second imaging condition to be different from a first imaging condition when the analysis result indicates a presence of a predetermined anomalous cell.

The apparatus for obtaining an image of a blood cell of a third aspect of the present invention includes: (a) an image obtainer for obtaining an image of a predetermined blood cell in a blood sample smeared on a sample holder; (b) an analysis result obtainer for obtaining a blood analysis result of the blood sample; and (c) a controller for controlling the image obtainer such that the image obtainer obtains a first number of the images when the analysis result indicates a number of a predetermined blood cell is larger than a predetermined value, and obtains a second number of the images, wherein the second number is smaller than the first number, when the analysis result indicates the number of the predetermined blood cell is smaller than the predetermined value.

The apparatus for obtaining an image of a blood cell includes: (a) a detector for detecting a predetermined blood cell in a blood sample smeared on a sample holder; (b) an image obtainer for obtaining a image of the predetermined blood cell detected by the detector; (c) an analysis result obtainer for obtaining a number of the predetermined blood cell; and (d) a controller for controlling the detector such that the detector detects the predetermined blood cell when the number obtained by the analysis result obtainer is larger than a predetermined value.

BRIEF DESCRIPTION OF THE DRAWINGS

FIG. 1 is a structural view of an examination system that includes an apparatus for analyzing blood images;

FIG. 2 is a block diagram of the blood analyzer;

FIG. 3 is a blood analysis result list related to WBC (white blood cell: nucleated blood cell);

FIG. 4 is a blood analysis list related to RBC (red blood cell);

FIG. 5 is a blood analysis list related to PLT (platelet);

FIG. 6 is a partial enlargement of a sample slide;

FIG. 7 is a perspective view of a sample slide and cassette;

FIG. 8 is a block diagram of an automatic microscope device and image processing device;

FIG. 9 is a block diagram of the automatic microscope controller;

FIG. 10 is a process flow chart of the automatic microscope controller;

FIG. 11 is a process flow chart of the image processing device;

FIG. 12 is a process flow chart of the imaging process;

FIG. 13 is a process flow chart of the white blood cell mode;

FIG. 14 is a process flow chart of the platelet mode;

FIG. 15 is a flow chart showing a modification of the 300 count imaging process;

FIG. 16 is a process flow chart of the automatic microscope controller;

FIG. 17 is a process flow chart of the image processing device; and

FIG. 18 is an example of a blood image.

DESCRIPTION OF THE PREFERRED EMBODIMENTS

An embodiment of the present invention is described in detail below with reference to the accompanying drawings.

General System Structure

In the present embodiment, a blood image analyzer 1, which images and analyzes blood, is offered as an example of an apparatus for imaging blood. FIG. 1 shows the general system structure that includes the blood imaging analyzer 1. This system is installed in a facility that performs blood examinations, such as a hospital or the like, and has various types of devices connected thereto via a network (LAN) 2.

Devices in this system in addition to the blood image analyzer 1 include a blood analyzer 3, sample preparation device 4, handling unit 5, host computer 6, comprehensive review terminal 7 and the like.

Structure of the Blood Analyzer

The blood analyzer 3 is configured as an automatic blood cell analyzer that measures predetermined items (multiple items) in blood and analyzes the results.

As shown in FIG. 2, the blood analyzer 3 is provided with a measuring part 31 for performing various measurements by RF/DC detection, sheath flow DC detection, flow cytometry using a semiconductor laser, SLS-hemoglobin method or the like, analysis part 32 for performing analyses based on the measurement results of the measuring part 31, and a determining part 33 for generating blood analysis result for predetermined determination items based on the analysis results.

The blood analyzer 3 is capable of performing various measurements related to blood via the measuring part 31.

Specifically, the measuring part 31 is capable of RBC/PLT measurements (counted via sheath flow DC detection) for measuring the number of red blood cells and number of platelets in blood, and HGB measurement (measured by the SLS-hemoglobin method) for measuring the amount of hemoglobin in blood, and the analyzing part 32 is capable of calculating the blood cell constants (average red blood cell volume, average red blood cell hemoglobin, average red blood cell hemoglobin concentration) based on the RGB, HGB, and HCT measurement results.

The measuring part 31 performs 4DIFF measurement (flow cytometric measurement) for fractionating and measuring groups of lymphocytes, monocytes, eosinophils, neutrophils, and basophils among white blood cells as WBC fractionation measurements, WBC/BASO measurement (flow cytometric measurement) for fractionating and measuring the number of white blood cells in blood and basophils among white blood cells, and IMI (immature information) measurement (RF/DC detection) that is a measurement of immature cell information.

The analyzing part 32 generates 4DIFF scattergrams, WBC/BASO scattergrams, and IMI scattergrams as WBC analyses.

The 4DIFF scattergram plots the side scattered light intensity on the X-axis and the side fluorescent light on the Y-axis via the flow cytometric method, and displays the fraction groups of red blood cell ghosts, lymphocytes, monocytes, eosinophils, neutrophils, and basophils.

The WBC/BASO scattergram plots the side scattered light intensity on the X-axis and the forward scattered light intensity on the Y-axis via flow cytometry, and displays the fraction groups of red blood cell ghosts, basophils among the white blood cells and other white blood cells (lymphocytes, monocytes, eosinophils, neutrophils).

The IMI scattergram shows a two-dimensional distribution of the size of the blood cells and the internal density of the blood cells (size of nucleus and the like), and allows for the discrimination of immature and mature white blood cells.

The measuring part 31 is capable of performing NRBC measurement (measurement by flow cytometry) to fractionate and measure the group of nucleated red blood cells among the blood cells, and the analyzing part 32 generates an NRBC scattergram as NRBC analysis.

The NRBC scattergram plots the side fluorescent light intensity on the X-axis and the forward fluorescent light on the Y-axis via the flow cytometric method, and displays the fraction groups of white blood cells and nucleated red blood cells.

The measuring part 31 performs RET measurement (measurement via flow cytometry) to fractionate and measure reticulocytes and platelets among blood cells, and the analyzing part 32 generates an RET scattergram as RET analysis.

The RET scattergram plots the side fluorescent light intensity on the X-axis and the forward fluorescent light on the Y-axis via the flow cytometric method, fractionates the mature red blood cells, reticulocytes, and platelets, and calculates the reticulocytes percentage, numbers of reticulocytes and red blood cells, and number of platelets.

The analyzing part 32 analyzes the RBC particle size distribution and analyzes the PLT particle size distribution.

The blood analyzer 3 generates blood analysis result that includes blood cell number information on nonwhite blood cells, and abnormal cell information that indicates the possibility of an occurrence of abnormal cells via the determining part 33 and based on the previously described measurements and analyses.

The generated blood analysis result is transmitted together with the analyzed sample ID (inherent identification information of the sample) from the blood analyzer 3 to the host computer 7, and the sample ID and blood analysis result are stored in the memory part (blood analysis result database) of the host computer.

Blood Analysis Result Generated by the Blood Analyzer

FIGS. 3 through 5 show lists of blood analysis result. The blood analysis result relates to the respective blood cells WBC (white blood cells), RBC (red blood cells), and PLT (platelets), and provides for each type blood cell a blood cell number information indicating the number of abnormal cells (mainly blood cells) ("Abnormal" in the item column in FIGS. 3 through 5), and abnormal cell information indicating the possibility of the occurrence of abnormal cells ("Suspect" in the item column in FIGS. 3 through 5).

The WBC and PLT abnormal cell information of FIG. 3 is described below after the conditions have been set for the WBC abnormal cell information (nucleation abnormality information) and PLT abnormal cell information (platelet clumps information).

Nucleated Blood Cell Information

The WBC abnormal cell information includes Blast? (blast cell), Immature Gran? (immature granulocyte), Left shift? (leftward shift), Atypical Lympho? (atypical lymphocyte), Abn Lympho/L-Blasts? (atypical lymphocyte and lymphoblast), NRBC? (nucleated red blood cell), RBC Lyse resistance? (poor hemolysis), and indicate the possibility of the occurrence of immature leukocytes that are normally not present in peripheral blood.

This information includes information indicating the possibility of the presence of NRBC (nucleated red blood cells; red blood cells do not normally have a nucleus) as abnormal cell information related to WBC, and may be called "abnormal nucleated blood cells" in abbreviation of immature leukocytes (which have a nucleus), atypical lymphocytes (which have a nucleus), and nucleated red blood cells.

Furthermore, the information indicating the possibility of the occurrence of immature leukocytes is referred to as immature white blood cell information, the information indicating the possibility of the occurrence of atypical lymphocytes is referred to as atypical lymphocyte information, and information indicating the possibility of the occurrence of nucleated red blood cells is referred to as nucleated red blood cell information, and these are all abbreviated as abnormal nucleated blood cell information.

As shown in FIG. 3, the abnormal nucleated blood cell information discriminates the possibility of the presence of abnormal nucleated blood cells by image patterns and the like in the DIFF scattergram and IMI scattergram; for example, when a scattergram can not be fractioned, or by dots appearing at a position at which they do not normally appear in a scattergram.

Platelet Clumps Information

PLT abnormal cell information (platelet clumps information) indicates the possibility of the occurrence of platelet clumps that is not normally generated and includes PLT clumps? (platelet clumps) and PLT clumps? (platelet clumps. The platelet clumps information is determined based on scattergrams and the like similar to abnormal nucleated blood cell information.

Blood Analysis Result Output

As described above, the generated abnormal nucleated blood cell information and the blood analysis result (IP message) that includes platelet clumps information and other information are transmitted from the blood analyzer 3 together with the analyzed sample ID (inherent identification information of the sample) to the host computer, and the sample ID and blood analysis result are stored in the memory part (blood analysis result database) of the host computer.

Sample Preparation Device and Handling Unit

The sample preparation unit 4 automatically prepares a blood sample preparation from the same sample analyzed by the blood analyzer 3. The sample preparation device 4 prepares a smear sample (wedge sample) by smearing a blood sample S on a sample slide 41, which is a sample carrier, as shown in FIGS. 6 and 7.

A sample memory part 41a configured by a two-dimensional code (two-dimensional barcode) is printed in the range of the sample preparation of the sample carrier (sample slide) 41. The two-dimensional code 41a includes at least information indicating a sample ID, and may also include patient name, date of measurement, and sample blood analysis result analyzed by the blood analyzer 3.

The sample memory part 41 is mechanically readable by a device (computer) other than the blood analyzer 3, and information needed for the sample can be obtained by reading the sample memory part 41.

The sample memory part 41 may also be configured by a unidimensional barcode, or other memory storage medium such as wireless data.

Information such as sample ID, patient name, date of measurement may be printable as humanly readable information 41b on the sample carrier 41.

The sample slide 41 with the smeared sample preparation is housed in the sample cassette 42 in the sample preparation device 4. The sample cassette 42 is transported to the blood image analyzer 1 by the handling unit 5.

Blood Image Analyzer Structure

Returning now to FIG. 1, the blood image analyzer 1 is provided with an automatic microscope device (main imaging device) 110 that has an imaging part for taking a blood image of the blood sample preparation of the sample, and an image processing device 120 for processing cell identification classifications and the like, and both devices 110 and 120 are mutually connected so as to be capable of communicating.

Automatic Microscope Device Structure

As shown in FIG. 8, the automatic microscope device 110 is provided with slide glass transporting part 11a for transporting the sample slide (slide glass) 41 delivered from the handling unit S within the automatic microscope device 110, and a slide glass transport drive part 111b for driving the transport part 111a.

When a cassette 42 is delivered to a predetermined position by the handling unit 5, the cassette 42 is detected by a cassette sensor 112a, and the sample slide 41 is removed from the cassette 42. Then, an ID reading part 112b acquires the information such as sample ID and the like by reading the two-dimensional code of the sample memory part 41a of the sample slide 41.

The sample slide 41 is placed on the stage 113a and the sample arranged on the stage 113a is magnified and observed via a microscope 114a, the subject blood cells (white blood cells) are detected by a WBC sensor 114b, and the stage 113a is moved to change the field of view via a stage drive circuit 113b. Image focus adjustment is performed by a focus drive circuit 115b based on an image detected by an auto focus unit 115a. At the same time, the image is captured by a color CCD camera 116a. An RGB color image is output from the CCD camera 116a, and image data are transmitted to the image processing device 120.

The imaging part of the present invention is configured by the CCD camera 116a, stage 113a, stage drive circuit 113b, auto focus unit 115a, and focus drive circuit 115b.

Various types of controls including the control of the imaging part in the automatic microscope device 110, and communication controls for data transmission to the network side via a network board 117 are accomplished by a automatic microscope control part 18.

The automatic microscope control part 118 is provided with a CPU 118a, ROM 118b, RAM 118c, I/O interface 118d, as shown in FIG. 9. The ROM 118b stores an operating system, control program for controlling the operation of the automatic microscope device 110, and data necessary for the execution of the control program. The CPU 118a can load the control program into the RAM 118c, or can execute the control program directly from the ROM 118b. Thus, the data that have been processed by the CPU 118a are sent to the various parts of the device 110 and devices external to the device 110 (image processing device 120 and the like) via the I/O interface 118d, and the data needed for processing by the CPU 118a are received from the various parts of the device 110 or from devices external to the device 110 (image processing device 120 and the like via the I/O interface 118d. The CPU 118a controls the operation of the automatic microscope device 110 by executing the control program.

Image Processing Device Structure

Returning now to FIG. 8, the image processing device (processor) 120 is provided with a CPU 121, ROM 122a, RAM 122b, display device 123 such as a CRT or the like, input devices such as a keyboard 124a, special keyboard 124b, mouse 124c and the like, host I/F 125, network board 126, and hard disk (memory part) 127. A printer 128 is connected to the image processing device 120.

In the image processing device 120, the RGB color image output from the automatic microscope device 110 is subjected to A/D conversion by an A/D converter 129a, and stored in an image memory 129b. The image stored in the image memory 129b is the object of processing by the CPU 121.

The ROM 122a stores an operating system, program for executing the processing performed by the image processing device 120, and data required for the execution of the program. The CPU 121 can load the program into the RAM 122b, or execute the program directly from the ROM 122a. Thus, the data that have been processed by the CPU 121 are sent to devices external to the device 120 (automatic microscope device 110 and the like) via the host I/F 125 or the network board 126, and the data needed for processing by the CPU 121 are received from the devices external to the device 120 (automatic microscope device 110 and the like) via the host I/F or network board 126.

The CPU 121 processes the image data, calculates the characteristics needed for identification classification of the blood cells, and identifies and classifies the blood cells based on these characteristics by executing the program.

The CPU 121 also displays the identification and classification results and the blood image on the CRT 123, and stores the blood image for review on the hard disk 127.

Imaging Process Flow 1

As shown in FIG. 10, when the sample cassette 42 is detected by the cassette sensor 112a of the automatic microscope device 110 (step S1-1), the sample slide 41 is removed from the cassette 42 step S1-2), the sample memory part 41a of the sample slide 41 is read (barcode reading( (step S1-3), and the sample ID (identification information) is obtained from the sample slide 41. The obtained sample ID is sent from the automatic microscope device 110 to the image processing device 120 (step S1-4), and the automatic microscope device 110 awaits reception of the imaging conditions (step S1-5).

As shown in FIG. 11, in the image processing device 120, when the sample ID (identification information) is received from the automatic microscope device 110 (step S2-1), the memory part (blood analysis result database) is referenced in the host computer 6 via the network 2, and the blood analysis result corresponding to the sample ID is obtained (step S2-2; blood analysis result obtainer).

Then, a determination is made as to whether or not abnormal cell information indicating a possibility of the occurrence of abnormal cells (Suspect Message) is contained in the obtained blood analysis result (IP message) (step S2-3).

If abnormal cell information is included in the blood analysis result, the imaging condition (first imaging condition relating to the blood cell count number) is set such that the blood cell count number that indicates the number of imagings for blood images set at a 100 count, and this imaging condition is sent to the automatic microscope device 110 (step S2-4).

When abnormal cell information is included in the blood analysis result, a determination is made as to whether or not the abnormal cell information (Suspect Message) relates to WBC (that is, whether or not abnormal nucleated blood cell information is included) (step S2-5).

When abnormal cell information (Suspect Message) related to WBC is not included, the imaging condition (first imaging condition related to blood cell count number; normal imaging condition) is set such that the blood cell count representing the number of blood cell imagings is set at a 100 count since a possibility of the presence of abnormal nucleated cells is not included, and the imaging condition is sent to the automatic microscope device 110 (step S2-4).

When abnormal cell information (Suspect Message) related to WBC is included, the imaging condition (second imaging condition related to blood cell count number; abnormal imaging condition) is set such that the blood cell count representing the number of blood cell imagings is set at a 300 count since there is a possibility of the presence of abnormal nucleated cells, and the imaging condition is sent to the automatic microscope device 110 (step S2-6).

Thus, the blood cell count of the imaging condition is set higher when blood analysis result indicates a possibility of an occurrence of abnormal nucleated cells than when there is no indication of a possibility of the occurrence of abnormal nucleated cells so as to obtain more blood images.

When abnormal cell information is included in the blood analysis result, a determination is made as to whether or not the abnormal cell information (Suspect Message) relates to PLT (that is, whether or not platelet clumps information is included) (step S2-7).

When the abnormal cell information (Suspect Message) does not include PLT information, the information is not sent to the automatic microscope device 110, and imaging is performed under an imaging condition (first imaging position related to the imaging position) at which imaging is only done at a first position (initial set position at the center or near center C of the sample (¼ the distance of the blood sample S from the edge part); refer to symbol C in FIG. 7) as a sample imaging position by the automatic microscope device 110 in a manner described later.

When the abnormal cell information (Suspect Message) does include PLT information, a second position (sample edge position; refer to symbol E in FIG. 7) is set as the sample imaging position (second imaging condition related to the imaging position) since platelet clumps has occurred, and this imaging condition is sent to the automatic microscope device 110 (step S2-8).

The imaging condition related to the blood cell count number and the imaging condition related to the imaging position may be transmitted to the automatic microscope device 110 separately as described above, or may be sent together.

Returning now to FIG. 10, when information of the imaging conditions (imaging condition related to the blood cell count number and/or imaging condition related to the imaging position) is received by the automatic microscope controller 117 of the automatic microscope device 110 (step S1-5), the sample slide 41 is transported to the stage 113a (step S1-6), and imaging is performed based on the received imaging conditions (step S1-7).

White blood cell mode imaging is performed (step S3-1) and platelet mode imaging (step S3-2) is performed as necessary, as shown in FIG. 12.

In the case of white blood cell imaging, the control part 118 discriminates the imaging condition related to the received blood cell count number (step S3-1-1), and if the imaging condition is a 100 count (first imaging condition), 100 white blood cell imagings are performed, whereas if the imaging condition is a 300 count (second imaging condition), 300 white blood cell imagings are performed, as shown in FIG. 13.

In the white blood cell mode, imaging is performed at the first position (initial set position at the center or near center C of the sample; refer to symbol C in FIG. 7).

Thus, when the blood analysis result indicates a possibility of the presence of abnormal nucleated cells, the blood cell count is increased for imaging such that the abnormal blood cells are reliably imaged. Moreover, the second imaging condition related to the blood cell count number is not necessarily a 300 count and may be any suitable count number.

In the platelet mode imaging process (step S3-2) that follows the white blood cell mode imaging process (step S3-1), a determination is made as to whether or not imaging is necessary (step S3-2-1). This determination is accomplished by whether or not an imaging condition related to the imaging position is included in the received imaging conditions.

When an imaging condition related to the imaging position is not included, execution of imaging in the platelet mode is unnecessary, and the mode ends without imaging being performed.

When an imaging condition related to the imaging position is included, the control part 118 controls the imaging part so as to perform imaging of the sample margin E as the platelet mode imaging (step S3-2-2). The sample margin E is a position that more readily has platelet clumps than the sample center C. The control part 118 moves the stage 113a via the stage drive circuit 113b and shifts the field of view to the margin E so as to image the margin E.

Thus, when a possibility of the presence of platelet clumps is indicated, the platelet clumps can be more reliably imaged by moving the field of view.

Imaging Processing Flow 2

As shown in FIG. 16, when the sample cassette 42 is detected by the cassette sensor 112a of the automatic microscope device 110 (step S5-1), the sample slide 41 is removed from the cassette 42 (step S5-2), the sample memory part 41a of the sample slide 41 is read (barcode reading) (step S5-3), and the sample ID (identification information) is obtained from the sample slide 41.

The obtained sample ID is sent from the automatic microscope device 110 to the image processing device 120 (step S5-4), and the automatic microscope device 110 awaits reception of the imaging conditions (step S5-5).

As shown in FIG. 17, in the image processing device 120, when the sample ID (identification information) is received from the automatic microscope device 110 (step S6-1), the memory part (blood analysis result database) is referenced in the host computer 6 via the network 2, and the blood analysis result corresponding to the sample ID is obtained (step S6-2; blood analysis result obtainer).

Then, the red blood cell number information is referenced in the obtained blood analysis result, and a determination is made as to whether or not the red blood cell number indicated in the red blood cell number information is less than a predetermined value (2 million/µL) (step S6-3). In the present embodiment, the predetermined value (normal standard for red blood cell number) is set as the number of red blood cells needed for auto focusing the automatic microscope device 110.

If the red blood cell number is less than the predetermined value, auto focusing of the automatic microscope device 110 is not performed since accurate imaging cannot be performed, and imaging termination information is set as the imaging condition information and sent to the automatic microscope device 110 so as to not perform wasteful imaging processes (step S-4).

When the number of red blood cells exceeds a predetermined value (when imaging), the white blood cell number information is referenced in the obtained blood cell analysis result and a determination is made as to whether or not the white blood cell number indicated in the white blood cell number information is less than a predetermined value (200 cells/µL). In the present embodiment, the predetermined value (normal standard of the white blood cell number) is set at a sufficient white blood cell number to obtain a blood cell imaging number (blood cell count number) needed for normal blood cell classification.

When the white blood cell number exceeds the predetermined value, the imaging condition (normal imaging condition; first imaging condition) is set such that the blood cell count number for indicating the white blood cell number included in the obtained blood image is set at 100 count, and this imaging condition is sent to the automatic microscope device 110 (step S6-6).

When the white blood cell number indicated in the white blood cell number information is less than the predetermined value, there are too few white blood cells in the sample and the blood cell count number is too high when it is the same as the normal imaging condition such that imaging is impractical in that imaging requires a long time. At this time the count number is set lower than the normal imaging condition at a 50 count (normal standard not met imaging condition; second imaging condition), and this imaging condition is sent to the automatic microscope device 110 (step S6-7).

Although the imaging termination information and imaging condition related to the blood cell count number are sent separately to the automatic microscope device 110 as described above, they may also be sent together.

Returning now to FIG. 16, when the automatic microscope control part 118 of the automatic microscope device 110 receives imaging condition information (imaging termination information and/or imaging information related to blood cell count number) (step S5-5), a determination is made as to whether or not imaging termination information is included in the imaging information (step S5-6).

When imaging termination information is included, the sample slide 41 is transported to and stored in the slide storage part (omitted from the drawing) of the automatic microscope device 110 with being imaged by the imaging part (step S5-7). Thus, samples that are difficult to image because the red blood cell number is too low for auto focusing are processed efficiently by not subjecting the sample to actual imaging and immediately processing the next sample.

When imaging termination information is not included, however, the sample slide 41 is transported to the imaging part (step S5-8), and imaged under the received imaging condition related to blood cell count number (step S5-9).

When imaging, the control part 118 discriminates the received imaging condition related to the blood cell count number, and controls the imaging part such that when the imaging condition is a 100 count (first imaging condition), imaging of white blood cells is performed 100 times (100 white blood cell images are taken), whereas when the imaging condition is a 50 count (second imaging condition), imaging of white blood cells is performed 50 times (50 white blood cell images are taken).

In the present embodiment, when a plurality of white blood cells are included in the image obtained by one imaging, only one white blood cell is extracted for classification, and the blood cell count number is [1]. In this case, the imaging number equals the blood cell count number.

When a plurality of white blood cells are included in the image obtained by one imaging, a plurality of white blood cells may be extracted for classification and the blood cell count number may be more than one. In this case, the imaging number is less than the blood cell count number, and the blood cell count number is obtained efficiently with fewer imagings.

Thus, when imaging using the second imaging condition in the present embodiment, it is possible to avoid the situation of taking a longer time for imaging more white blood cells when there are fewer white blood cells because fewer imagings are needed than under the first imaging condition.

FIG. 18 shows an example of an obtained image with a single white blood cell W near the center of the image. A plurality of red blood cells R are present around the white blood cell. Auto focusing is accomplished based on the red blood cells present around the white blood cell.

Blood Cell Classification Process

The obtained blood cell image (sample image; white blood cell digital image) is sent to the image processing device 120, and the image processing device performs blood cell (white blood cell) characteristic extraction processing and blood cell (white blood cell) classification processing based on the sample image.

The characteristics extraction process is performed by separating pixels equivalent to the nucleus and pixels equivalent to the cytoplasm in the sample image of the white blood cell from other pixels.

The classification process identifies the types of object blood cells using feature parameters related to the nucleus and feature parameters related to cytoplasm, and classifies the blood cells of the blood cell count number.

The white blood cell (nucleated blood cell) classification process classifies the object blood cells as six types of mature white blood cells (stab neutrophil, segmented neutrophil, eosinophil, basophil, lymphocyte, monocyte) and erythroblasts. The six types of mature white blood cells are normal nucleated blood cells, and three types of immature leukocytes, and erythroblasts are abnormal nucleated blood cells.

When the blood analysis result of the blood analyzer 3 indicates a possibility of the presence of abnormal nucleated blood cells as described above, the blood cell count number is increased and the number of classification object blood cells is increased to allow accurate detection and classification of the abnormal nucleated blood cells.

Furthermore, when the blood analysis result of the blood analyzer 3 indicates the possibility of the presence of platelet clumps, the platelet clumps can be handled to avoid reporting a low platelet value due to the agglutination by imaging the sample margin part in which platelet clumps is easily discovered.

The obtained image and classification result are sent together with the sample ID from the blood image analyzer 1 to the host computer 6, and are stored in the host computer 6. The blood analysis result, obtained images, and blood cell classification results stored in the host computer 6 can be viewed on the comprehensive review terminal 7.

FIG. 15 shows a modification of the 300 count imaging process (imaging process under the second imaging condition related to blood cell count number; step S3-1-3) of FIG. 13.

When the received imaging condition related to the blood cell count number is the second imaging condition (300 count), the automatic microscope control part 118 first performs imaging under the first imaging condition (100 count) related to the blood cell count number (step S401).

The count number is set at 100 (blood cell count number of the first imaging condition (step S4-2), the sample is the information is sent to the image processing device 120, and the count is increased 1 (step S4-3).

In the image processing device 120, the sample image is received and stored in a memory such as a RAM or the like (step S4-4), and the blood cell (white blood cell) classification process is performed based on the sample image. The classification result is stored in memory (step S4-6) and sent to the automatic microscope device 110 side (step S4-7).

When the imaged blood cell classification result is received (step S4-8), the automatic microscope control part 118 determines whether or not the classification result is an abnormal nucleated blood cell.

When the imaged blood cell is an abnormal nucleated blood cell, further imaging is suspended and the imaging under the second imaging condition related to blood cell count number ends.

When the imaged blood cell is not an abnormal nucleated blood cell, the process returns to step S4-4 and imaging is repeated until the count value attains the blood cell count value of the second imaging condition (300 count).

According to this process, since imaging is performs until at least one abnormal nucleated blood cell is included in the classification result during imaging under the second imaging condition related to blood count number, it is possible to reliably image an abnormal nucleated blood cell with relatively few imagings. Moreover, when imaging under the second imaging condition, the number of imagings equal to the imagings under the first imaging condition (first blood count number=100) is ensured, and a number of sample images required for classification is also ensured.

When imaging under the second imaging condition, a maximum value of the blood count number is set (second blood count number=100), and imaging is stopped when the imaging number attains the maximum value even if an abnormal nucleated cell is not included in the classification result, thus preventing unending imaging.

The present invention is not limited to the previously described embodiment.

For example, conditions related to whether or not to image may be added to the imaging conditions related to blood cell count number and imaging conditions related to imaging position. Such a condition related to whether or not to image may to add a condition stipulating that imaging is unnecessary due to a high degree of abnormality when information indicating a high degree of abnormality such as blasts? (blast cells) are included as WBC abnormal cell information (Suspect Message) so as to perform human microscopic observation without imaging by the blood image analyzer 1.

Conversely, a condition may be added that stipulates imaging is unnecessary when the blood analysis result lacks any indication of the possibility of a presence of abnormal cell information, since the need for analysis is low due to the low degree of abnormality.

Such conditions related to whether or not imaging is needed can be determined prior to the processing of steps S3-1-1 of FIG. 13.

Although the blood imaging device 1 obtains sample blood analysis result from a host computer in the above embodiment, such information may also be obtained from the blood analyzer 3. Furthermore, when the sample memory part (two-dimensional code) 41a of the sample slide 41 stores blood analysis result, such information may also be obtained from the sample memory part 41a.

In the above embodiment, when abnormal cell information (Suspect Message) is included in the WBC, the possibility of a presence of abnormal nucleated cells is indicated, and the second imaging condition is set to set the blood cell count number indicating the number of blood cell images to be taken at a 300 count. However, a second imaging condition may differ and be set in accordance with the types of abnormal cell information present in plurality. For example, when the suspect Message is Blasts?, the blood cell count number may be set at a 200 count, and when the Suspect Message is Immature Gran?, the blood cell count may be set at a 400 count.

The blood analysis result that includes the white blood cell number information, red blood cell number information also may be obtained by the blood image analyzer 1 itself. For example, a sample may be imaged by the imaging part of the blood image analyzer 1 at a relatively wide field of view to generate blood analysis result that includes the white blood cell number (distribution density of the white blood cells) and red blood cell number (distribution density of the red blood cells) in the sample, and the imaging conditions may then be set based on the generated blood analysis result.

What is claimed is:

1. An apparatus for obtaining images of a blood cells, comprising:
    an image obtainer for obtaining images of predetermined blood cells in a blood sample smeared on a sample holder;
    an analysis result obtainer for obtaining an analysis result of the blood sample, wherein the analysis result has been obtained by a blood analyzer which has analyzed blood cells in the blood sample; and
    a controller for controlling the image obtainer such that the image obtainer obtains the images under a first imaging condition when the obtained analysis result does not include abnormal cell information that indicates a presence of an anomalous nucleated blood cell, and obtains the images under a second imaging condition to be different from the first imaging condition when the obtained analysis result includes the abnormal cell information.

2. The apparatus according to claim 1, further comprising:
    a detector for detecting a nucleated blood cells as the predetermined blood cells, wherein the image obtainer obtains the image of the predetermined blood cells detected by the detector.

3. The apparatus according to claim 1, wherein the anomalous nucleated blood cell is selected from the group consisting of an immature leukocyte, an atypical lymphocytes, a nucleated red blood cell ,and combinations of thereof.

4. The apparatus according to claim 1, wherein the first imaging condition relates to a first number of images, the second imaging condition relates to a second number of images, the second number of images is larger than the first number.

5. The apparatus according to claim 1, wherein the controller judges whether the anomalous nucleated blood cell is present in the images obtained by the image obtainer.

6. The apparatus according to claim 5, wherein, under the second imaging condition, the controller controls the image obtainer such that the image obtainer stops obtaining a next image, when the anomalous nucleated blood cell is present in the images obtained by the image obtainer.

7. The apparatus according to claim 6, wherein, under the second imaging condition, the controller controls the image obtainer such that the image obtainer stops obtaining a next image, when a predetermined number of the predetermined blood cells are obtained by the image obtainer.

8. The apparatus according to claim 7, wherein the first imaging condition relates to a first number of images, and the predetermined number is larger than the first number.

9. The apparatus according to claim 5, wherein the anomalous nucleated blood cell is selected from the group consisting of an immature leukocyte, an atypical lymphocyte, a nucleated red blood cell, and combinations of thereof.

10. The apparatus according to claim 1, wherein the analysis result obtainer obtains the analysis result from the blood analyzer.

11. The apparatus according to claim 1, wherein the sample holder comprises an identification part which identifies the blood sample and indicates the analysis result of the blood sample.

12. The apparatus according to claim 11, wherein the identification part comprises a two-dimensional code.

13. The apparatus according to claim 1, wherein the predetermined blood cells includes white blood cells.

14. An apparatus for obtaining images of blood cells, comprising:
- an image obtainer for obtaining images of predetermined blood cells in a blood sample smeared on a sample holder;
- an analysis result obtainer for obtaining an analysis result of the blood sample, wherein the analysis result has been obtained by a blood analyzer which has analyzed blood cells in the blood sample; and
- a controller for controlling the image obtainer such that the image obtainer obtains the images under a first imaging condition when the obtained analysis result does not include abnormal cell information that indicates a presence of aggregated platelets, and obtains the images under a second imaging condition to be different from the first imaging condition when the obtained analysis result includes the abnormal cell information,
- wherein the first imaging condition relates to a first position on the sample holder for obtaining the images, the second imaging condition relates to a second position on the sample holder for obtaining the images; and
- wherein the second position has higher probability of presence of the aggregated platelets than the first position.

15. The apparatus according to claim 14, wherein the first position is a center or adjacent to the center of the blood sample on the holder, the second is a margin part of the blood sample on the holder.

16. A method for obtaining images of blood cells comprising:
- obtaining a blood analysis result of a blood sample, wherein the analysis result has been obtained by a blood analyzer which has analyzed blood cells in the blood sample; and
- obtaining images of a predetermined blood cells in a blood sample smeared on a sample holder under a first imaging condition or a second imaging condition to be different from the first imaging condition;
- wherein the images are obtained under the first imaging condition when the obtained analysis result does not include abnormal cell information that indicates a presence of an anomalous nucleated blood cell, and obtained under the second imaging condition when the obtained analysis result includes the abnormal cell information.

17. An apparatus for obtaining images of blood cells comprising:
- an image obtainer for obtaining images of predetermined blood cells in a blood sample smeared on a sample holder;
- an analysis result obtainer for obtaining a blood analysis result of the blood sample, wherein the analysis result has been obtained by a blood analyzer which has analyzed blood cells in the blood sample; and
- a controller for controlling the image obtainer such that the image obtainer obtains a first number of the images under a first imaging condition when a number of the predetermined blood cells included in the analysis result is larger than a predetermined value, and obtains a second number of the images under a second imaging condition, wherein the second number is smaller than the first number, when the number of the predetermined blood cells is smaller than the predetermined value.

18. The apparatus according to claim 17, wherein the predetermined blood cells includes white blood cells.

19. An apparatus for obtaining images of blood cells comprising:
- an image obtainer for obtaining a images of predetermined blood cells in a blood sample smeared on a sample holder;
- an analysis result obtainer for obtaining a blood analysis result of the blood sample, wherein the analysis result includes a number of red blood cells and has been obtained by a blood analyzer which has analyzed blood cells in the blood sample; and
- a controller for controlling the image obtainer such that the image obtainer obtains images of the predetermined blood cells under a first imaging condition when the number of the red blood cells included in the analysis result is larger than a predetermined value and the image obtainer does not obtain images of the predetermined blood cells under a second imaging condition when the number of the red blood cells is not larger than the predetermined value.

20. The apparatus according to claim 19, wherein the predetermined blood cells includes white blood cells.

* * * * *